United States Patent
Sos

(10) Patent No.: US 9,427,252 B2
(45) Date of Patent: *Aug. 30, 2016

(54) THROMBUS REMOVAL AND INTRAVASCULAR DISTAL EMBOLIC PROTECTION DEVICE

(71) Applicant: Thomas A. Sos, New York, NY (US)

(72) Inventor: Thomas A. Sos, New York, NY (US)

(*) Notice: Subject to any disclaimer, the term of this patent is extended or adjusted under 35 U.S.C. 154(b) by 227 days.

This patent is subject to a terminal disclaimer.

(21) Appl. No.: 14/289,027

(22) Filed: May 28, 2014

(65) Prior Publication Data

US 2015/0025555 A1    Jan. 22, 2015

Related U.S. Application Data

(60) Provisional application No. 61/828,264, filed on May 29, 2013.

(51) Int. Cl.
*A61B 17/221* (2006.01)
*A61B 17/3207* (2006.01)
*A61B 17/22* (2006.01)

(52) U.S. Cl.
CPC ......... *A61B 17/3207* (2013.01); *A61B 17/221* (2013.01); *A61B 2017/2212* (2013.01); *A61B 2017/2215* (2013.01); *A61B 2017/22094* (2013.01)

(58) Field of Classification Search
CPC A61B 17/22; A61B 17/221; A61B 17/3207; A61B 2017/22094; A61B 2017/2212; A61B 2017/2215
See application file for complete search history.

(56) References Cited

U.S. PATENT DOCUMENTS

| | | |
|---|---|---|
| 5,662,671 A | 9/1997 | Barbut et al. |
| 5,759,173 A | 6/1998 | Preissman et al. |
| 5,848,964 A | 12/1998 | Samuels |
| 5,895,399 A | 4/1999 | Barbut et al. |
| 5,947,995 A | 9/1999 | Samuels |
| 5,993,469 A | 11/1999 | McKenzie et al. |
| 5,997,557 A | 12/1999 | Barbut et al. |
| 6,010,522 A | 1/2000 | Barbut et al. |
| 6,129,739 A | 10/2000 | Khosravi |
| 6,168,579 B1 | 1/2001 | Tsugita |
| 6,179,851 B1 | 1/2001 | Barbut et al. |
| 6,245,087 B1 | 6/2001 | Addis |

(Continued)

OTHER PUBLICATIONS

U.S. Appl. No. 14/550,289, filed Nov. 21, 2014, Sos.

(Continued)

*Primary Examiner* — Ryan J Severson
(74) *Attorney, Agent, or Firm* — Wilson, Sonsini, Goodrich & Rosati

(57) ABSTRACT

A clot extraction catheter comprises an expandable tubular mesh, a tapered tip fixed to the tubular mesh distal end, a self-expanding rim attached to the tubular mesh proximal end, at least three control wires, an inner sheath, and an outer sheath advancable over the inner sheath. To extract a clot, the catheter is advanced through the clot. The inner sheath is retracted relative to the control wires and the tubular mesh, allowing the rim and the tubular mesh to expand. The tubular mesh is retracted to capture the clot, closed once the clot is captured, constrained proximally by the distal portion of the inner sheath, and retracted with the inner sheath into the outer sheath. The control wires may be manipulated to control the angle of the rim relative to the longitudinal axis of the sheaths, facilitating clot capture and retraction of the tubular mesh into the sheaths thereafter.

24 Claims, 8 Drawing Sheets

(56) References Cited

U.S. PATENT DOCUMENTS

| | | |
|---|---|---|
| 6,309,399 B1 | 10/2001 | Barbut et al. |
| 6,391,044 B1 | 5/2002 | Yadav et al. |
| 6,428,552 B1 | 8/2002 | Sparks |
| 6,494,895 B2 | 12/2002 | Addis |
| 6,530,939 B1 | 3/2003 | Hopkins et al. |
| 6,620,148 B1 | 9/2003 | Tsugita |
| 6,620,182 B1 | 9/2003 | Khosravi et al. |
| 6,682,543 B2 | 1/2004 | Barbut et al. |
| 6,695,865 B2 | 2/2004 | Boyle et al. |
| 6,755,813 B2 | 6/2004 | Ouriel et al. |
| 6,755,846 B1 | 6/2004 | Yadav |
| 6,824,545 B2 | 11/2004 | Sepetka et al. |
| 6,893,431 B2 | 5/2005 | Naimark et al. |
| 6,918,921 B2 | 7/2005 | Brady et al. |
| 6,964,672 B2 | 11/2005 | Brady et al. |
| 6,974,469 B2 | 12/2005 | Broome et al. |
| 7,014,647 B2 | 3/2006 | Brady et al. |
| 7,037,320 B2 | 5/2006 | Brady et al. |
| 7,097,440 B2 | 8/2006 | Papp et al. |
| 7,306,618 B2 | 12/2007 | Demond et al. |
| 7,311,661 B2 | 12/2007 | Heinrich |
| 7,479,153 B2 | 1/2009 | Belef |
| 7,481,788 B2 | 1/2009 | Naimark et al. |
| 7,608,087 B1 | 10/2009 | Addis |
| 7,731,722 B2 | 6/2010 | Lavelle et al. |
| 7,799,051 B2 | 9/2010 | Brady et al. |
| 7,927,349 B2 | 4/2011 | Brady et al. |
| 7,938,798 B2 | 5/2011 | Naimark et al. |
| 7,976,560 B2 | 7/2011 | Denison et al. |
| 7,993,363 B2 | 8/2011 | Demond et al. |
| 8,002,790 B2 | 8/2011 | Brady et al. |
| 8,083,762 B2 | 12/2011 | Kusleika et al. |
| 8,114,115 B2 | 2/2012 | Brady et al. |
| 8,377,092 B2 | 2/2013 | Magnuson |
| 8,444,665 B2 | 5/2013 | Tsugita |
| 8,486,105 B2 | 7/2013 | Demond et al. |
| 2001/0016755 A1 | 8/2001 | Addis |
| 2002/0072764 A1 | 6/2002 | Sepetka et al. |
| 2002/0082639 A1 | 6/2002 | Broome et al. |
| 2002/0099397 A1 | 7/2002 | Sparks |
| 2002/0120287 A1 | 8/2002 | Huter |
| 2002/0123761 A1 | 9/2002 | Barbut et al. |
| 2002/0133191 A1 | 9/2002 | Khosravi et al. |
| 2002/0161393 A1 | 10/2002 | Demond et al. |
| 2002/0165576 A1 | 11/2002 | Boyle et al. |
| 2003/0073979 A1 | 4/2003 | Naimark et al. |
| 2003/0097114 A1 | 5/2003 | Ouriel et al. |
| 2003/0130684 A1 | 7/2003 | Brady et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2004/0006370 A1 | 1/2004 | Tsugita |
| 2004/0082962 A1 | 4/2004 | Demarais et al. |
| 2005/0004595 A1 | 1/2005 | Boyle et al. |
| 2005/0043756 A1 | 2/2005 | Lavelle et al. |
| 2005/0049619 A1 | 3/2005 | Sepetka et al. |
| 2005/0165280 A1 | 7/2005 | Heinrich |
| 2005/0177106 A1 | 8/2005 | Naimark et al. |
| 2005/0209634 A1 | 9/2005 | Brady et al. |
| 2006/0122644 A1 | 6/2006 | Brady et al. |
| 2006/0122645 A1 | 6/2006 | Brady et al. |
| 2006/0229658 A1 | 10/2006 | Stivland |
| 2006/0241681 A1 | 10/2006 | Brady et al. |
| 2007/0100373 A1 | 5/2007 | Magnuson et al. |
| 2007/0208374 A1 | 9/2007 | Boyle et al. |
| 2007/0233179 A1 | 10/2007 | Brady et al. |
| 2007/0233180 A1 | 10/2007 | Brady et al. |
| 2007/0233183 A1 | 10/2007 | Brady et al. |
| 2008/0058860 A1 | 3/2008 | Demond et al. |
| 2008/0109031 A1 | 5/2008 | Sepetka et al. |
| 2009/0105722 A1 | 4/2009 | Fulkerson et al. |
| 2009/0131882 A1 | 5/2009 | Naimark et al. |
| 2010/0168785 A1 | 7/2010 | Parker |
| 2011/0125181 A1 | 5/2011 | Brady et al. |
| 2011/0137334 A1 | 6/2011 | Anderson et al. |
| 2011/0160741 A1 | 6/2011 | Asano et al. |
| 2011/0166586 A1 | 7/2011 | Sepetka et al. |
| 2011/0264135 A1 | 10/2011 | Demond et al. |
| 2012/0172915 A1 | 7/2012 | Fifer et al. |
| 2012/0330346 A1 | 12/2012 | Frimerman |
| 2012/0330350 A1 | 12/2012 | Jones et al. |
| 2013/0253467 A1 | 9/2013 | Gianotti et al. |
| 2013/0310803 A1 | 11/2013 | Morsi |
| 2015/0297251 A1 | 10/2015 | Sos |

OTHER PUBLICATIONS

"Office action dated Dec. 31, 2015 for U.S. Appl. No. 14/550,289."
International search report and written opinion dated Oct. 22, 2014 for PCT/US2014/039843.
International search report and written opinion dated Feb. 24, 2015 for PCT Application No. US2014/066925.

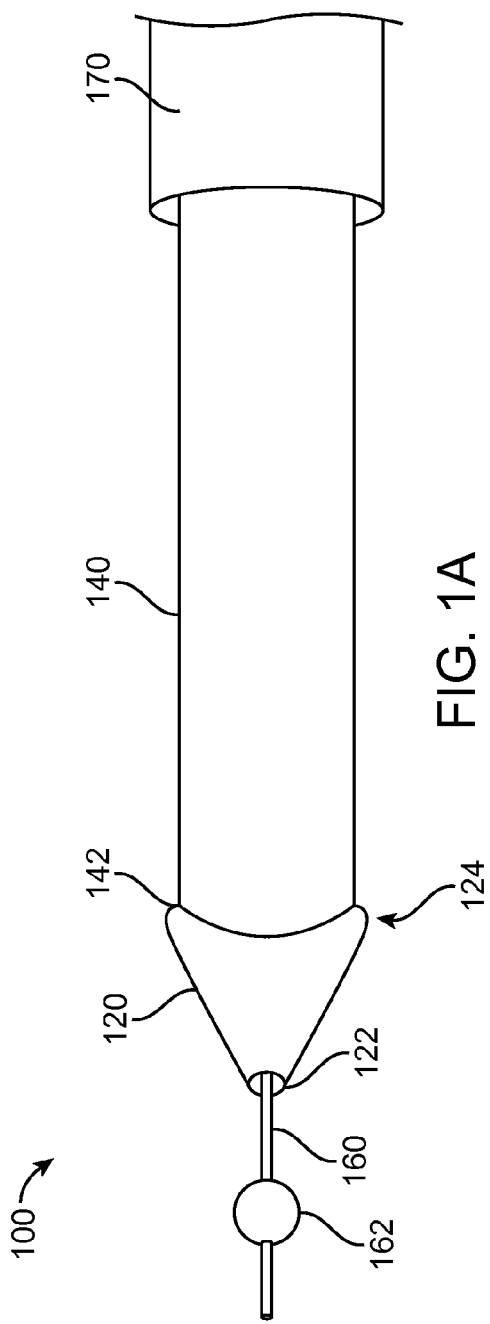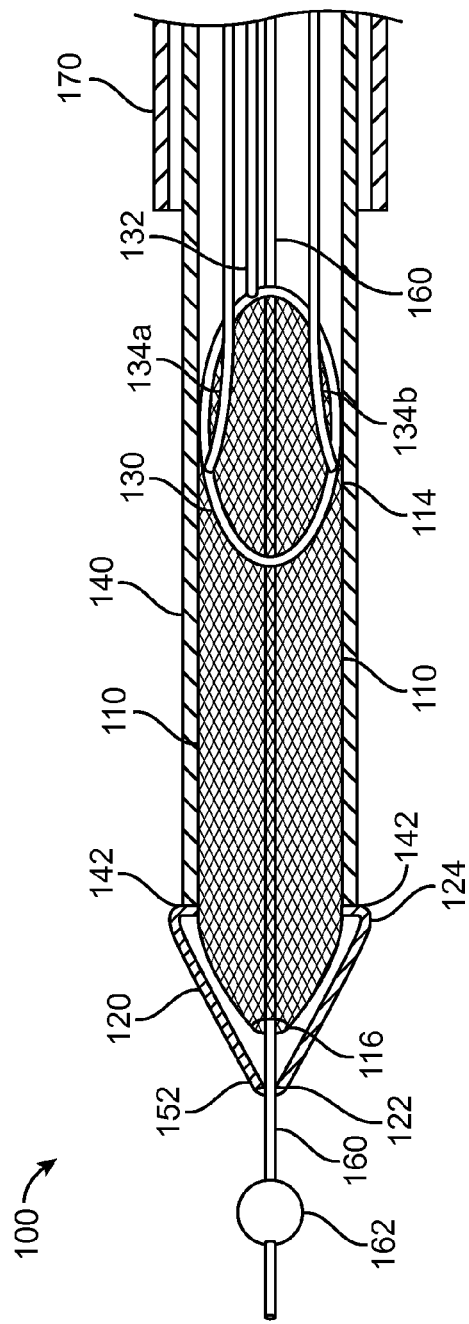

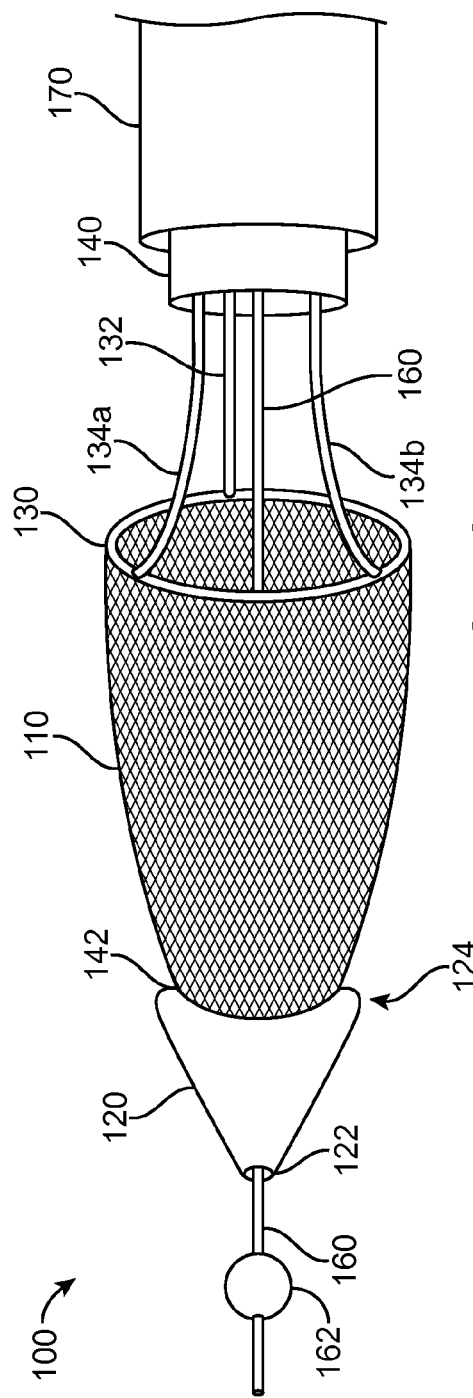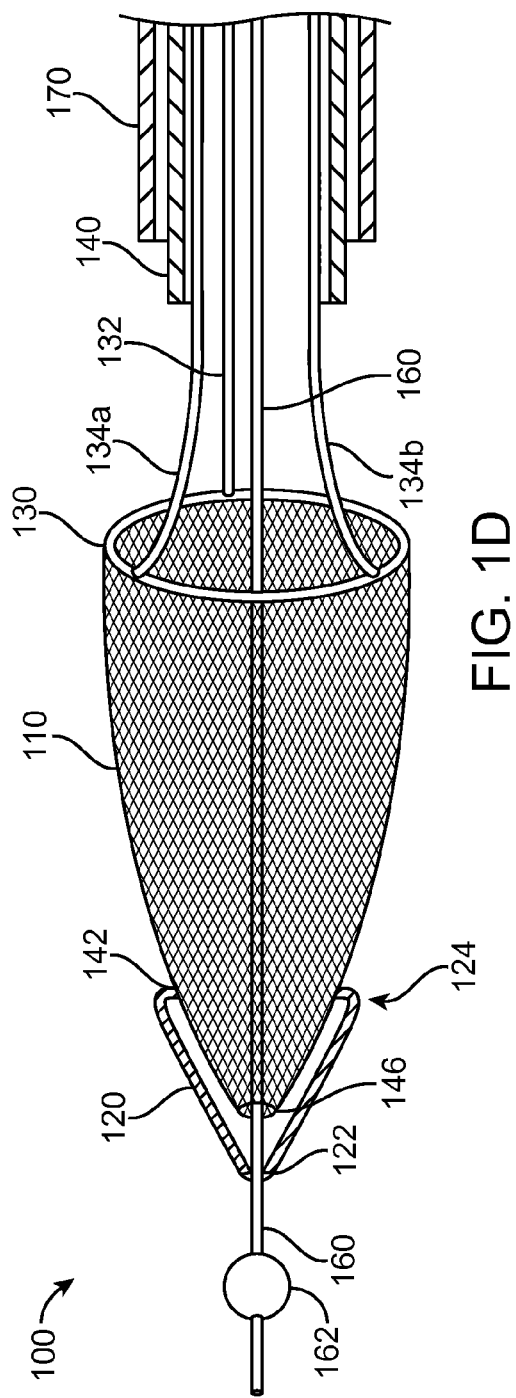

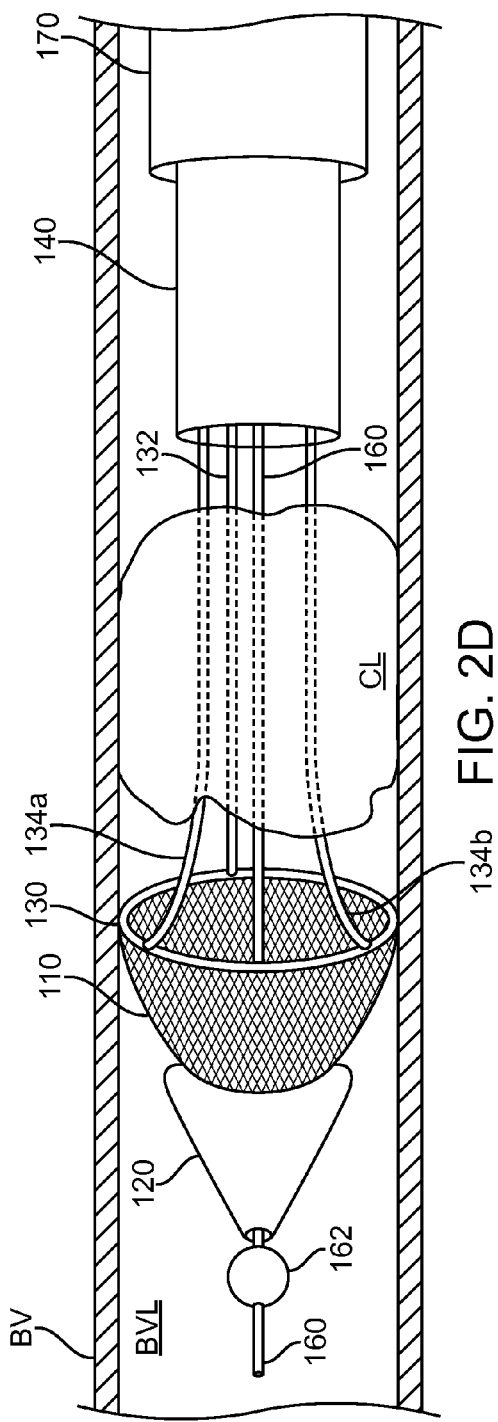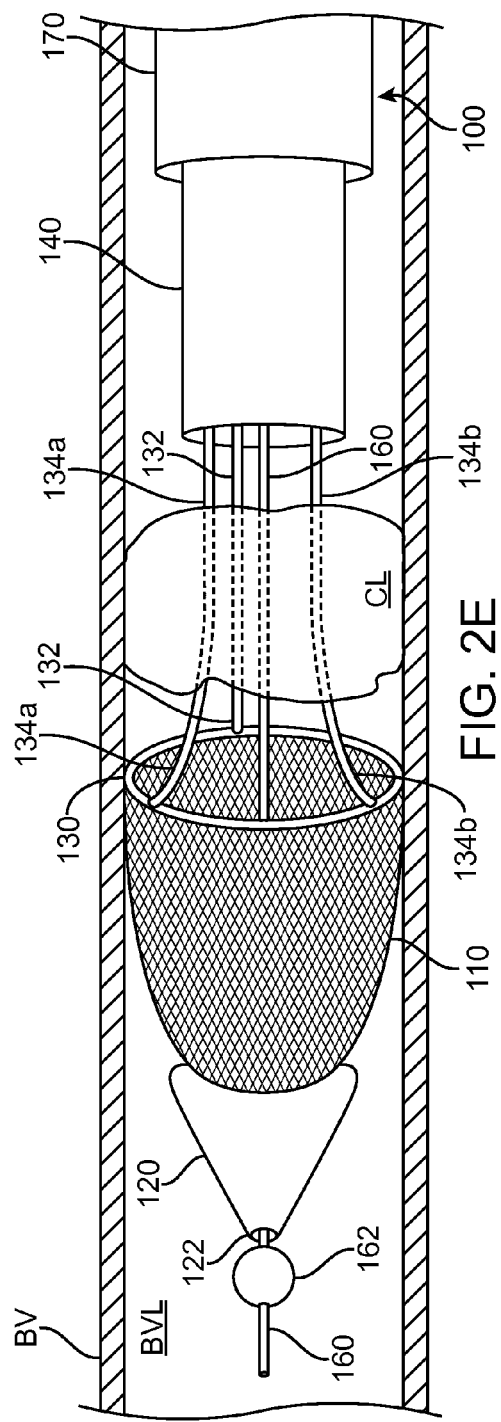

THROMBUS REMOVAL AND INTRAVASCULAR DISTAL EMBOLIC PROTECTION DEVICE

CROSS-REFERENCE

This application claims the benefit of U.S. Provisional Application No. 61/828,264, filed May 29, 2013, which application is incorporated herein by reference.

BACKGROUND

The present disclosure generally relates to medical devices, systems, and methods. In particular, the present disclosure generally relates to the removal of intravascular or intracavitary thrombus or other material which may frequently require removal to restore blood flow or other normal functionality of the organ system affected.

Typically, blood clot or emboli to the pulmonary arteries of the lung, the brain, the peripheral arteries of the extremities, in the venous system, or in dialysis access vessels are potentially life and/or limb threatening conditions. These clots are typically cleared when medically indicated by either pharmacological (thrombolytic and/or anticoagulant drugs) or mechanical means or a combination of the two. Thrombolytic drugs typically require several hours to days to accomplish dissolving these clots. Frequently, there is not sufficient "warm" ischemic time for the target organ to permit such a long time to reperfusion. Thrombolytic drugs also have an approximately 5% incidence of major complications such as hemorrhage and stroke. Currently available mechanical devices may not be effective in the presence of large volumes of thrombus or may have a very large diameter and may be stiff. Thus, these devices may be difficult or impossible to advance into curved and tortuous vessels such as the pulmonary arteries. Some lime the "Hydrolyzer" devices available in the marketplace may break up a clot and suction the resulting particles out, but may infuse large volumes of fluid as part of their action. Such infusion may be physiologically difficult to handle for the patient. Others, like "AngioVac" may require a miniature veno venous cardiovascular bypass to allow filtering out of the suctioned thrombus and return of the cleared blood to the patient. Most of these devices may also hemolyze blood, which may result in damage to the kidneys and may also cause distal emboli.

For these reasons, emergency open surgical thrombectomy, which in itself may have a high mortality and morbidity, is often employed as a last resort, especially for large pulmonary emboli. There are therefore needs for devices which can rapidly and safely extract large volumes of blood clot or other materials with little or no adjuvant use of thrombolytic drugs. Such devices may be used during intravascular interventions to prevent distal embolization by capture of blood clots or atheromatous material.

References which may be of interest include U.S. Pat. Nos. 8,377,092, 7,479,153, 6,494,895, and 7,976,560 and U.S. Patent Application Publication Nos. 2012/0330350 and 2012/0330346.

SUMMARY

The present disclosure provides medical devices, systems, and methods for the removal of intravascular or intracavitary thrombus or other material.

Aspects of the present disclosure provide clot extraction catheters. A clot extraction catheter may comprise an expandable tubular mesh, a tapered tip, a self-expanding rim, at least three control wires, and an inner sheath. The expandable tubular mesh may have a distal end and a proximal end. The expandable tubular mesh may have an expanded configuration and a constrained configuration. The tapered tip may be fixed to the distal end of the expandable tubular mesh. The self-expanding ring may be attached to the proximal end of the expandable tubular mesh. The self-expanding rim may have an unconstrained diameter which is greater than a width of the proximal end of the tapered tip. The control wires may be attached to the self-expanding rim. The inner sheath may be advancable over the control wires to constrain at least a portion of the self-expanding rim and at least a portion of the tubular mesh within a lumen of the inner sheath. The control wires can be manipulated to control the angle of the self-expanding rim relative to the longitudinal axis of the inner sheath when the self-expanding rim is unconstrained. The clot extraction catheter may further comprise an outer sheath advancable over the inner sheath.

The proximal end of the tapered tip may have a rounded lip to reduce interference as the catheter is drawn proximally through a bodily lumen or cavity.

The control wires may comprise a main wire and two chord wires. The main wire may be translatable proximally and distally. The two chord wires may be translatable proximally and distally independently from the primary wire. The wires may be independently translated proximally and/or distally to control the angle of the self-expanding rim relative to the axis of the inner sheath when the self-expanding rim is unconstrained. The two chord wires may comprise a first chord wire and a second chord wire each independently translatable proximally and distally. In some embodiments, the main control wire may be fixed and the two chord wires may be independently translatable proximally and distally. The control wires may also be used to rotate the clot extraction catheter to adjust its orientation within a bodily vessel or cavity. The control wires may be attached to the rim directly or one or more of the control wires may be coupled to a nipple or protrusion from the rim. In some embodiments, the control wires may each comprise proximal portions which are fixed to one another.

The control wires may be retracted proximally to capture a clot or thrombus once the self-expanding rim and expandable tubular mesh is advanced and positioned distally of the clot or thrombus. The expandable tubular mesh, once capturing the blood clot, may be closed by advancing the inner sheath over the control wires and at least a portion of the expandable tubular mesh. Alternatively or in combination, the inner sheath may be advanced over the control wires and at least a portion of the expandable tubular mesh. In some embodiments, the two chord control wires are advanced further than the main wire to change the angle of the rim to a more obtuse angle relative to the longitudinal axis of the inner sheath to facilitate advancement of the inner sheath over the control wires. The expandable tubular mesh and the captured clot or thrombus may be gradually molded to the inner diameter of the inner sheath and/or the outer sheath. While very chronic and organized thrombus may resist deformation and molding, such clots may crumble in the expandable tubular mesh when withdrawn into the inner shaft and/or the outer sheath.

In some embodiments, the distal end of the inner and/or outer sheaths may be flared and/or may be configured to flare to accommodate the tubular mesh and the captured clot or thrombus therein. For example, the sheath(s) may comprise partial depth slits parallel to the longitudinal axis of the sheath(s) at the distal end of the sheath(s) or the wall of the sheath(s) may be gradually thinner toward the distal end to allow expansion of the sheath diameter.

The distal end of the expandable tubular mesh may be substantially closed and the proximal end of the expandable tubular mesh may be open. The expandable tubular mesh may be made of mylar, nitinol, or some other resilient and/or expandable material. The length, diameter, and/or pore size of the expandable tubular mesh may vary according to a desired specific task or other factors. Such tasks or factors may include the clot burden to be removed, the diameter of the vessel to be treated, etc.

The expandable tubular mesh may have a pore size. For clot removal, the tubular mesh may have a pore size sufficiently large to allow normal blood cells not to be captured and sufficiently small to allow thrombus to be captured. For distal embolic protection, the pore size may sufficiently large to allow normal blood cells not to be captured and sufficiently small to allow atheroemboli as small as 20 microns, frequently as small as 10 microns, to be captured.

The inner sheath may be retractable mounted over the expandable tubular mesh to constrain the tubular mesh in the constrained configuration. The inner sheath may be distally advanced to engage the proximal end of the tapered tip to circumscribe and constrain the expandable tubular mesh and may be proximally retracted to release the expandable tubular mesh from constraint so that the mesh self-expands into the expanded configuration.

The clot extraction catheter may further comprise an inner pusher tube advancable within the inner sheath. The inner pusher tube, when advanced, may be disposed within the lumen of the inner sheath and in-between the control wires. The pusher tube may comprise a guidewire lumen through which a guidewire can be passed through. The pusher tube may be used to facilitate advancement of the clot extraction catheter through a subject's vasculature to reach a clot. The pusher tube may facilitate advancement of the clot extraction catheter through tortuous vasculature. For example, the pusher tube may be used to advance the clot extraction catheter through a femoral artery, through the inferior vena cava (IVC), and through the right atrium and ventricle of the heart to reach a pulmonary artery. Alternatively or in combination, the clot extraction catheter may be advanced through this tortuous vasculature without the aid of the inner pusher tube. The clot extraction catheter and its component elements such as the inner sheath may be sufficiently flexible and compliant such that it may navigate through the tortuous vascular while accommodating for the twists and turns of the vasculature and while minimizing the exertion of any damaging force to the vessel walls.

Aspects of the present disclosure may further provide a system for extracting clot from a blood vessel. The system may comprise the clot extraction catheter as described herein. The system may further comprise a guidewire advancable within the inner sheath of the clot extraction catheter. The guidewire may comprise a bulb near a distal end of the guidewire and may also comprise a soft, floppy tip distal to the bulb. The bulb of the guidewire may be used to facilitate retraction of the tubular mesh and/or inner sheath. The distal end of the tapered tip distal of the tubular mesh may abut the bulb as the guidewire is retracted. Afterwards, further retraction of the guidewire may additionally retract the tubular mesh and/or inner sheath. The guidewire may be used to facilitate the advancement of the clot extraction catheter through a subject's vasculature to reach a clot. The guidewire may first be advanced through the vasculature to reach a target location before the clot extraction catheter is advanced over the guidewire. For example, the guidewire and/or clot extraction catheter may be introduced into the vasculature initially through a jugular or femoral vein before reaching the superior vena cava (SVC) or inferior vena cava (IVC), respectively.

When used as a clot retrieval device, the clot extraction catheter described herein can be used in conjunction with a distal embolic protection device.

Aspects of the disclosure also provide methods for extracting a clot from a bodily vessel or cavity. A distal end of a tapered tip of a clot extraction catheter may be positioned in a lumen of the bodily vessel or cavity proximal of a clot. The tapered tip may be advanced past the clot such that a proximal end of the tapered tip is distal of the clot. A rim coupled to a proximal end of a tubular mesh of the clot extraction catheter may be opened to open the proximal end of the tubular mesh. The tubular mesh may be retracted proximally to capture the clot within the tubular mesh. The rim may be closed to close the proximal end of the tubular mesh and enclose the captured clot within the tubular mesh. The clot extraction catheter may then be removed from the lumen of the bodily vessel or cavity.

An angle of the opened rim relative to a shaft of the clot extraction catheter may also be adjusted before or during retracting of the tubular mesh to capture the clot. This adjustment may be made by proximally or distally translating a main control wire of the clot extraction catheter coupled to the rim independently from proximally or distally translating at least two chord control wires of the clot extraction catheter. Alternatively or in combination, this adjustment may be made by proximally or distally translating a first chord control wire of the at least two chord control wires independently from proximally or distally translating a second chord control wire of the at least two chord control wires.

The rim coupled to the proximal end of the tubular mesh may be opened to allow the rim to self-expand. To allow the rim to self-expand, an inner sheath of the clot extraction catheter may be retracted relative to the rim. Alternatively or in combination, the rim may be advanced out of the inner sheath. To close the rim and enclose the captured clot within the tubular mesh, the tubular mesh may be retracted proximally at least partially into a lumen of the inner sheath. Further, the outer sheath may be used to enclose the tubular mesh with the captured clot (for example, where the inner sheath only partially encloses the tubular mesh with the captured clot). The outer sheath may be advanced over the tubular mesh with the captured clot to fully enclose the tubular mesh before the clot extraction catheter is removed from the bodily vessel or lumen. Alternatively or in combination, the tubular mesh with the captured clot may be retracted proximally into a lumen of the outer sheath.

To position the distal end of the tapered tip of a clot extraction catheter in the lumen of the bodily vessel or cavity proximal of a clot, the clot extraction catheter may be distally advanced with a pusher tube. Alternatively or in combination, a guidewire may be advanced through the bodily vessel or cavity and advancing the clot extraction catheter over the guidewire.

The clot extraction catheter described herein may be used to extract clot, thrombus, or other materials in a bodily vessel or cavity. This bodily vessel or cavity may comprise a blood vessel such as a vein, an artery, the aorta, a pulmonary artery, a vena cava, an inferior vena cava (IVC), a superior vena cava (SVC), an internal jugular vein, an external jugular vein, a subclavian vein, a hepatic vein, a renal vein, an iliac vein, a common iliac vein, an internal iliac vein, an external iliac vein, a femoral vein, or a peripheral vein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A shows a side view of a clot extraction catheter having its tubular mesh clot capture basket constrained, in accordance to many embodiments;

FIG. 1B shows a side sectional view of the clot extraction catheter of FIG. 1A having its tubular mesh clot capture basket constrained;

FIG. 1C shows a side view of the clot extraction catheter of FIG. 1A having its tubular mesh clot capture basket unconstrained;

FIG. 1D shows a side sectional view of the clot extraction catheter of FIG. 1A having its tubular mesh clot capture basket unconstrained; and FIGS. 2A to 2K show sectional views of the clot extraction catheter of FIG. 1A in use to remove a clot or thrombus in a blood vessel.

DETAILED DESCRIPTION

Figure 2A:
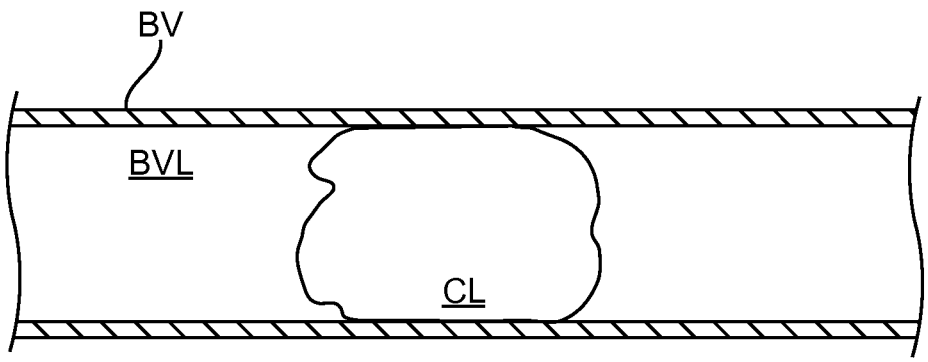

FIGS. 1A to 1D show a clot extraction catheter 100 according to many embodiments. FIGS. 1A and 1B show the clot extraction catheter 100 with its tubular mesh or clot capture basket 110 in a constrained, delivery configuration. The tubular mesh or clot capture basket 110 may be self-expanding and may comprise a shape-memory material or metal such as Nitinol (NiTi). The clot extraction catheter 100 comprises a tubular inner sheath 140 which is advancable over the tubular mesh 110 to constrain the tubular mesh 110. The tubular inner sheath 140 can be retracted proximally to release the tubular mesh 110 as shown in FIGS. 1C and 1D. When unconstrained, the tubular mesh 110 may resiliently assume its unconstrained configuration which may be in the form of a tube sock-like structure. Alternatively or in combination, the tubular mesh 110 may comprise a heat-based shape memory material so that the unconstrained tubular mesh 110 may assume the tube sock-like structure when exposed to body temperatures in a bodily vessel or cavity. The clot extraction catheter 100 may further comprise an outer sheath 170 which may be advanced over the tubular inner sheath 140 (or the tubular inner sheath 140 may be retracted to be within the outer sheath 170). The outer sheath 170 may have a width or diameter of 8-25 Fr, for example. The inner sheath 140 and/or outer sheath 170 may comprise proximal side arms (e.g., for the passage of a guidewire, fluid infusion, etc.) and/or injection ports. The inner sheath 140 and/or outer sheath 170 may also be provided with one or more radiopaque markers to facilitate locating the inner sheath 140 and/or outer sheath 170 as they are advanced through the vasculature.

The clot extraction catheter 100 may further comprise an atraumatic, dilator tip 120. The dilator tip 120 may elongate and tapered with a straight surface to facilitate the passage of the tip 120 through a clot without pushing the clot. The dilator tip has a distal end 122 and a proximal end 124. The proximal end 124 may be rounded so that the dilator tip 120 is atraumatic when proximally retracted. The width or diameter of the dilator tip 120 at the proximal end 124 may be slightly greater than the width or diameter of the tubular inner sheath 140. The distal end 142 of the tubular inner sheath 140 may abut the proximal end 124 of the dilator tip 120 when distally advanced. The proximal end 124 of the dilator tip 120 may be attached or fixed to a distal portion 112 of the tubular mesh 110. The outer sheath 170 may have a width or diameter such that it may be advanced over the dilator tip 120. In some embodiments, the outermost diameter of the dilator tip 120 may match the innermost diameter of the distal end of the outer sheath 170 such that the dilator tip 120 may be fitted to the distal end of the outer sheath 170 when retracted. Alternatively or in combination, the distal end of the outer sheath 170 may be flared.

The distal portion 112 of the tubular mesh 110 may be tapered. This tapering may end at the distal end 116 of the tubular mesh 110. The distal end 116 of the tubular mesh 110 may be coupled to the dilator tip 130. The distal end 122 of the dilator tip 120 may be coupled to the distal end 116 of the tubular mesh 110 as well. A guidewire 160 may be passed through the lumen of the inner sheath 140 and disposed in-between the control wires 132, 134a, 134b. The guidewire 160 may have a diameter of 0.025 inches, for example. The guidewire 160 may comprise a bullet or bulb 162 near the distal end of the guidewire 160. The bullet or bulb 162 may have a width or diameter greater than that of the distal end 122 of the dilator tip 120 such that distal advancement of the clot extraction catheter 100 may be limited. The clot extraction catheter 100 may be distally advanced until the distal end 122 of the dilator tip 120 abuts the bullet or bulb 162. The bullet or bulb 162 may have a diameter of 0.035 inches, for example. The bullet or bulb 162 may also facilitate in the navigation of the guidewire 160 through tortuous vasculature as well facilitate advancement of the guidewire 160 through clot, thrombus, emboli, or the like in a bodily vessel or lumen.

The open proximal end 114 of the tubular mesh 110 may be coupled to a ring 130. The ring 130 may be self-expanding. When unconstrained by the inner sheath 140, the ring 130 may resiliently expand to facilitate the opening and expansion of the tubular mesh 110. The ring 130 may comprise a shape-memory material such as Nitinol (NiTi) to facilitate self-expansion. The shape-memory material may be heat-based, for example, so that the ring 130 may assume its expanded configuration when exposed to bodily temperatures in a bodily vessel or cavity.

At least three control wires 132, 134a, 134b may be coupled to the ring 130. The control wires may comprise a main control wire 132 and two chord wires 134a, 134b. The control wires 132, 134a, 134b may be disposed within the inner sheath 140 and run the length of the clot extraction catheter 100 proximally from the ring 130. The control wires 132, 134a, 134b may be independently manipulated at a proximal, handle end of the clot extraction catheter 100. The main control wire 132 may be translated either distally or proximally independently from the distal or proximal translation of the two chord wires 134a, 134b. In some embodiments, each of the chord wires 134a, 134b may be independently translated from each other as well. The control wires 132, 134a, 134b may be manipulated to change the angle of the expanded rim 130 relative to the longitudinal axis of the inner sheath 140. The attachment points of the control wires 132, 134a, 134b may be evenly distributed over the circumference of the rim 130. The control wires 132, 134a, 134b may have a width of 0.010 inches, for example. In some embodiments, the chord wires 134a, 134b may be thinner than the main wire 132. In alternative embodiments, two or more of the control wires 132, 134a, 134b may be attached to one another at proximal portions thereof such that they may be user manipulated in conjunction. Also, while three control wires are shown in FIGS. 1A to 1D, alternative number of control wires (such as one, two, or four or more) may be provided instead.

FIGS. 2A to 2K show the clot extraction catheter 100 in use to capture a clot CL in the lumen BVL of a blood vessel BV. The blood vessel BV may be selected from the group comprising a vein, an artery, a pulmonary artery, a vena cava, an inferior vena cava (IVC), a superior vena cava (SVC), an internal jugular vein, an external jugular vein, a subclavian vein, a hepatic vein, a renal vein, an iliac vein, a common iliac vein, an internal iliac vein, an external iliac vein, a femoral vein, a peripheral vein, and a peripheral artery, for example. The clot extraction catheter 100 may also be used to capture other solid, biological material in other bodily vessels or cavities such as the ureter, urethra, renal pelvis, bladder, intestines, esophagus, stomach, small intestines, large intestines, colon, vagina, uterus, trachea, and bronchus, to name a few.

Figure 2B:
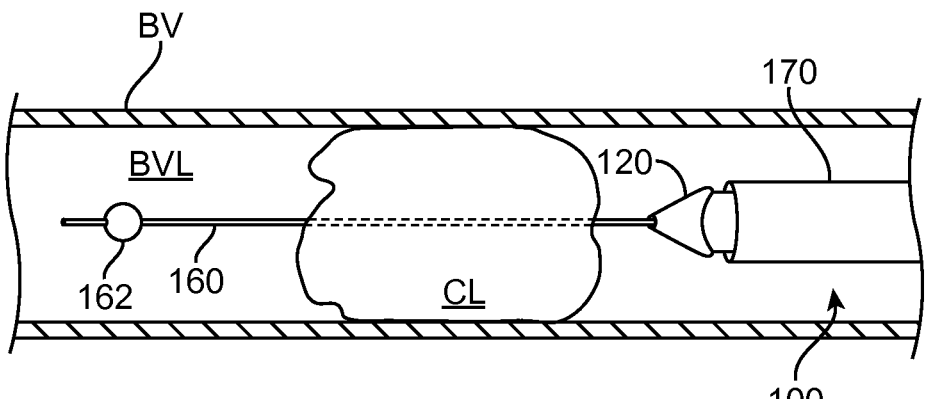

As shown in FIG. 2A, a blood vessel lumen BVL may have a clot CL lodged therein. In some embodiments, a diagnostic catheter and guidewire may be passed through the clot CL, followed by an exchange of the diagnostic catheter with the guidewire 160 as shown in FIG. 2B. In some embodiments, an angioplasty catheter may be advanced through clot CL either through the diagnostic catheter or the guidewire 160 and the clot CL may be expanded to facilitate the later advancement of the clot extraction catheter 100 therethrough.

As shown in FIG. 2B, the guidewire 160 and bulb 162 may be advanced through the clot CL. The clot extraction catheter 100 may be advanced over the guidewire 160 to be positioned just proximally of the clot CL. At this point, most of the elements of the clot extraction catheter 100 remain housed within the outer sheath 170. The tapered, dilator tip 120 may be exposed.

Figure 2C:
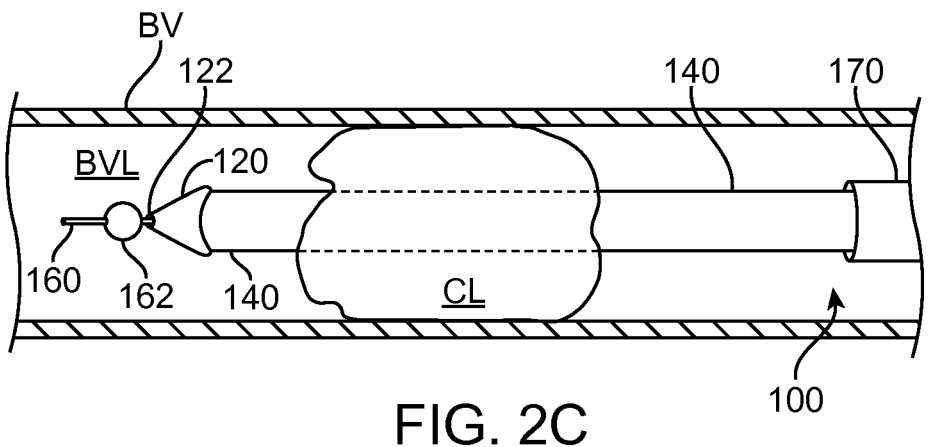

As shown in FIG. 2C, the clot extraction catheter 100 may be advanced through the clot CL. In particular, the inner sheath 140 and the dilator tip 120 may be advanced from the outer sheath 170 through the clot CL. The inner sheath 140 and the dilator tip 120 may be advanced through the clot CL until the distal end 122 of the dilator tip 120 abuts the bulb 162 of the guidewire 160.

As shown in FIG. 2D, the inner sheath 140 may now be retracted proximally and/or the tubular mesh 100 and the self-expanding ring 130 advanced distally so that the tubular mesh 110 and the self-expanding ring 130 are unconstrained and expanded just distal of the clot CL. The tubular mesh 110 of the clot extraction catheter may be telescoped up to itself to shorten the mesh 100 beyond the clot, e.g., by advancing the tapered tip 120 to the bulb 162 and pushing the rim 130 forward toward the bulb 162. The guidewire 160 with the bulb 162 may also be pulsed proximally to pull the dilator tip 120 proximally to facilitate the telescoping and shortening of the tubular mesh 110.

As shown in FIG. 2E, the inner sheath 140 may instead be retracted proximally and/or the tubular mesh 110 and the self-expanding ring 130 advanced distally so that the tubular mesh 110 and the self-expanding ring 130 are unconstrained and expanded with little or no telescoping. The expanded tubular mesh 110 and ring 130 may be positioned immediately distal of the clot CL.

Figure 2F:
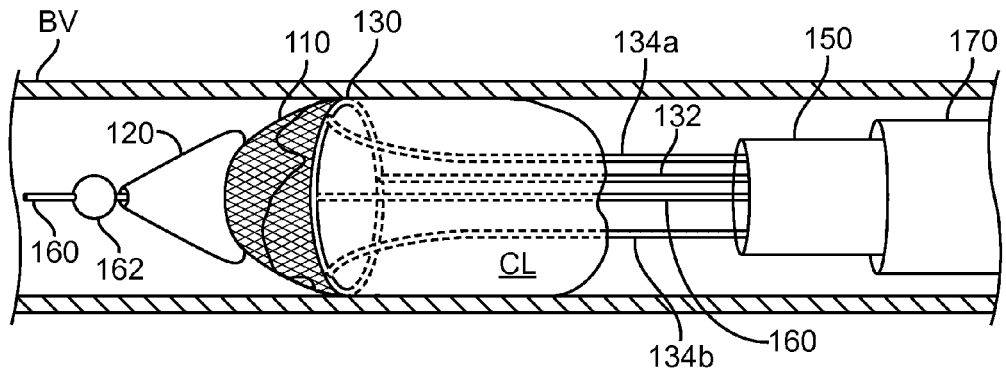
Figure 2G:
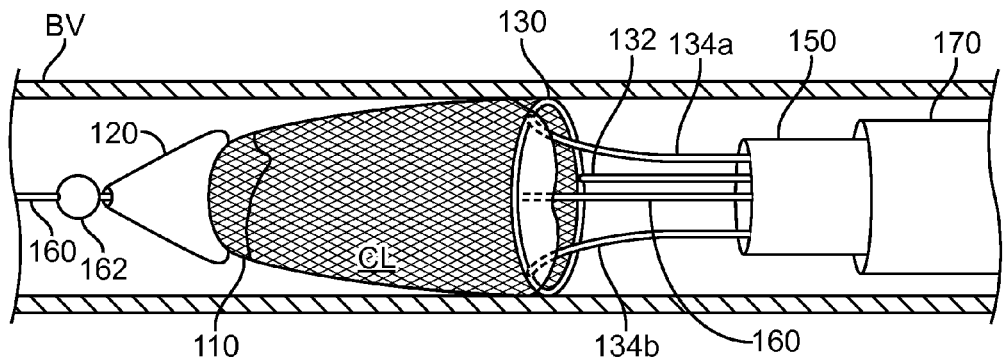

As shown in FIGS. 2F and 2G, the expanded tubular mesh 110 may be proximally retracted partially as shown in FIG. 2F and then completely as shown in FIG. 2G to capture the clot CL within the tubular mesh 110. The tubular mesh 110 may proximally retracted by proximally retracting one or more of the main control wire 132, or the two chord wires 134a, 134b.

Figure 2H:
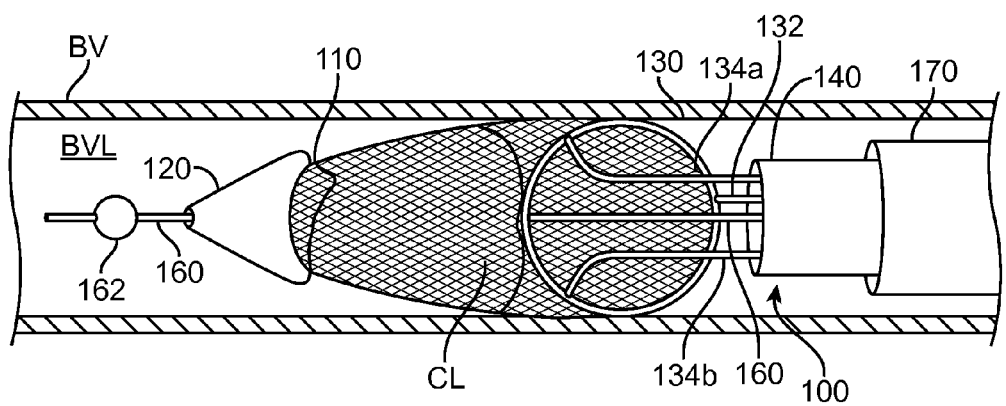
Figure 2I:
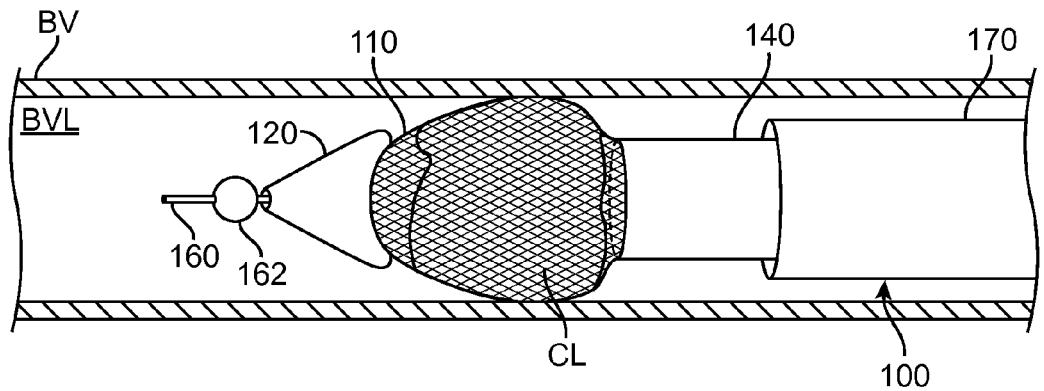

As shown in FIGS. 2H and 2I, the angle of the rim 130 relative to the longitudinal axes of the inner sheath 140 and/or outer sheath 170 may be controlled to facilitate capture of the clot CL or the retraction of the tubular mesh 110 and the rim 130 first constrained by the distal portion of the inner sheath 140 and back within the outer sheath 170. The rim 130 angle may be initially be 0° as shown in FIGS. 2E to 2G but may be manipulated to be 45° as shown in FIG. 2H. This angle may be controlled by manipulating one or more of the control wires 132, 134a, or 134b. As shown in FIG. 2H, the two chord control wires 134a, 134b may be advanced distally and/or the main control wire 132 may be retracted proximally to control the angle. By providing three or more control wires, the rim 130 angle may be controlled with two or more degrees of freedom. Alternatively or in combination, the clot extraction catheter 100 may be rotated to control the orientation of the rim 130 and the tubular mesh 110. In other embodiments, the control wires 132, 134a, 134b may have a fixed orientation relative to one another such that the rim 130 angle may be fixed (such as to 45°, for example.)

As shown in FIG. 2I, the rim and the tubular mesh 110, including the clot CL captured therein, may be proximally retracted partially into the inner sheath 140 (i.e., the proximal portion of the tubular mesh 110 may be retracted into and constrained by the inner sheath 140). This may partially or completely close the rim 130 and the mesh 110. In some embodiments, the distal end of the inner sheath 140 may be flared and/or may become flared as the tubular mesh 110 and the captured clot CL are retracted to facilitate such retraction.

Figure 2J:
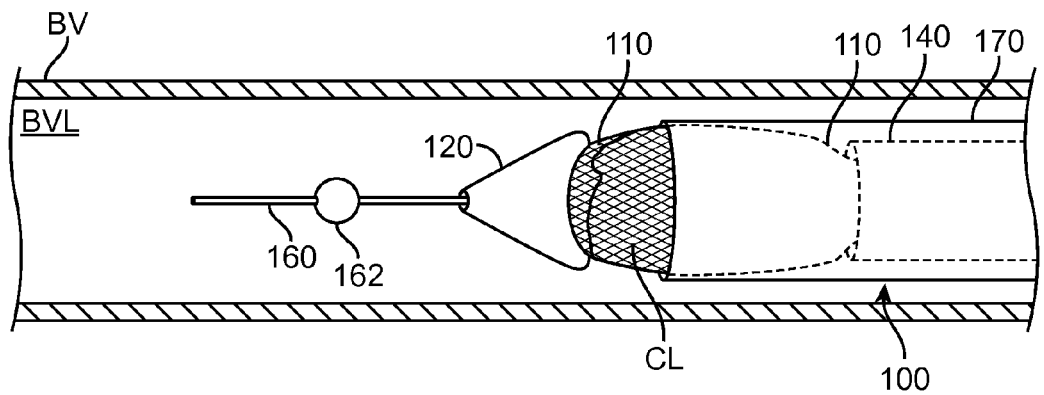

As shown in FIG. 2J, as the captured clot CL is retracted into the outer sheath 170, the outer sheath 170 may change the shape of the clot CL and may break apart or cause the crumbling of the larger particles of the clot CL. The captured clot CL, the tubular mesh 110, and the inner sheath 140 may be fully retracted into the outer sheath such that the clot extraction catheter assumes the configuration shown by FIG. 2B.

Figure 2K:
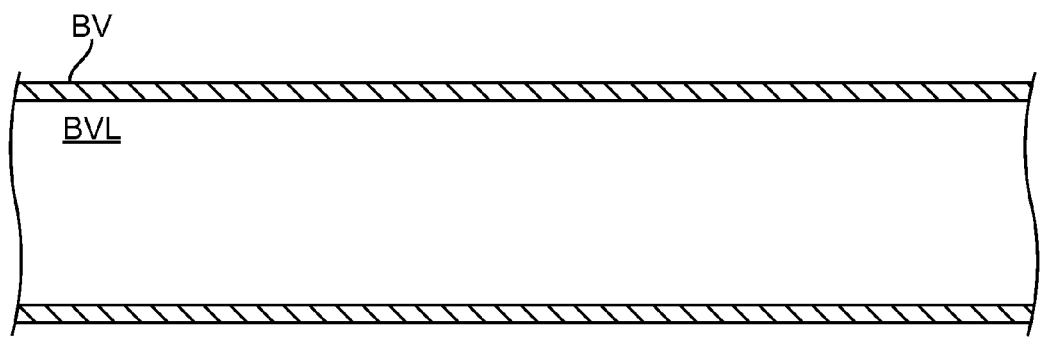

As shown in FIG. 2K, the clot extraction catheter 100 and the guidewire 160 may then be removed from the blood vessel BV to leave the blood vessel lumen BVL free and clear of any clot. If further clot extraction may be necessary, the guidewire 160 and the outer sheath 170 may both be left in place and only the inner sheath 140 and clot extraction catheter 100 with the captured clot CL removed. The amount of clot removed can be ascertained by introducing a diagnostic catheter over the guidewire 160 and contrast angiography performed over the wire. The clot extraction catheter and the inner sheath 140 may be cleaned and reinserted into the outer sheath 170, or a new different sized clot extractor 100 and its inner sheath 140 may be introduced.

Figure 3:
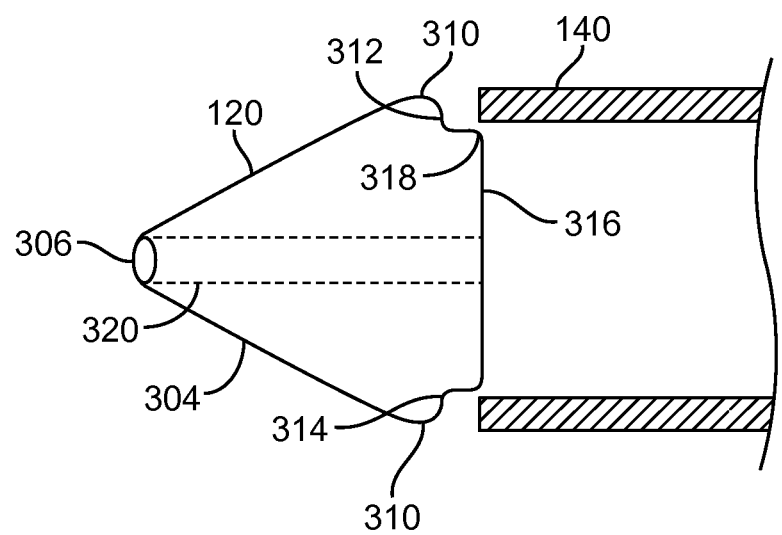
FIG. 3 illustrates a partial cross-section of the dilator tip.

FIG. 3 illustrates an exemplary embodiment of the dilator tip 120 positioned adjacent the inner sheath 140. The dilator tip 120 and the inner sheath 120 may be any of the embodiments disclosed in this specification. The dilator tip 120 includes a conical tapered outer surface 304, a distal guidewire port 306, guidewire lumen 320 and a proximal end that cooperates with the distal end of the inner sheath 140. The proximal end of the dilator tip 120 includes smooth radius outer edge 310 to minimize vascular trauma during retraction of the dilator tip 120. Flat shoulder 312 provides a stop against which the distal end of inner sheath 140 may rest. Also, a flat proximal end 316 facilitates self-centering of the inner sheath 140 when engaged with the proximal end of the dilator tip 120 Inner edges 314, 318 also have radii in order to prevent vascular trauma and provide a smooth, self-centering transition so that inner sheath 140 is easily advanced and aligned with the proximal end of the dilator tip 120.

Figure 4:
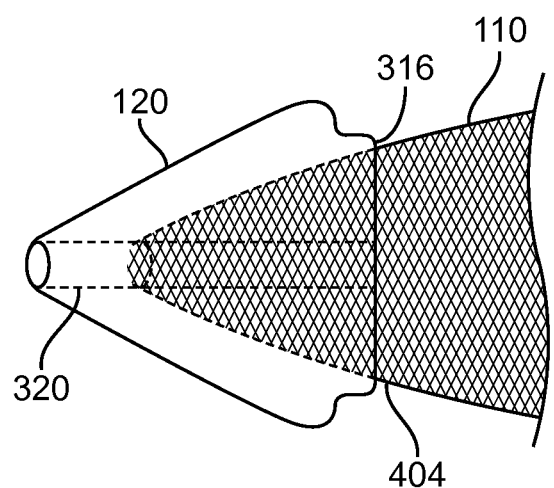
FIG. 4 illustrates the tubular mesh coupled to the dilator tip.

FIG. 4 illustrates the tubular mesh 110 disposed in the dilator tip 120. The tubular mesh and the dilator tip may be any of the embodiments disclosed herein. The tubular mesh 110 preferably has a width 404 adjacent the proximal end of dilator tip 120 that is less than the width of the flat proximal end 316. This minimizes the possibility of the tubular mesh 110 being trapped or caught by the distal end of inner sheath 140 (not illustrated).

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the disclosure. It should be understood that various alternatives to the embodiments of the disclosure described herein may be employed in practicing the invention. It is intended that the following claims define the scope of the invention and that methods and structures within the scope of these claims and their equivalents be covered thereby.

What is claimed is:

1. A clot extraction catheter comprising:
   an expandable tubular mesh having a distal end and a proximal end, the tubular mesh having an expanded configuration and a constrained configuration;
   a tapered tip fixed to the distal end of the expandable tubular mesh;
   a self-expanding ring attached to the proximal end of the expandable tubular mesh, the self-expanding ring having an unconstrained diameter which is greater than a width of the proximal end of the tapered tip;
   at least three control wires attached to the self-expanding ring;
   an inner sheath advancable over the at least three control wires to constrain at least a portion of the self-expanding ring and at least a portion of the tubular mesh within a lumen of the inner sheath,
   wherein the at least three control wires can be manipulated to control the angle of the self-expanding ring relative to an axis of the inner sheath when the self-expanding ring is unconstrained.

2. The clot extraction catheter as in claim 1, further comprising an outer sheath advancable over the inner sheath.

3. The clot extraction catheter as in claim 1, wherein the proximal end of the tapered tip has a rounded lip to reduce interference as the catheter is one or more of advanced distally or retracted proximally through a bodily lumen or cavity.

4. The clot extraction catheter as in claim 1, wherein the at least three control wires comprises a main wire translatable proximally and distally and two chord wires translatable proximally and distally independently from the primary wire to control the angle of the self-expanding ring relative to the axis of the shaft when the self-expanding ring is unconstrained.

5. The clot extraction catheter as in claim 4, wherein the two chord wires comprises a first chord wire and a second chord wire each independently translatable proximally and distally to control the angle of the self-expanding ring relative to the axis of the shaft when the self-expanding ring is unconstrained.

6. The clot extraction catheter as in claim 4, wherein the at least three control wires each comprise proximal portions which are fixed to one another.

7. The clot extraction catheter as in claim 1, wherein the distal end of the expandable tubular mesh is open to allow a guidewire to be passed therethrough.

8. The clot extraction catheter as in claim 1, wherein proximal end of the expandable tubular mesh is open.

9. The clot extraction catheter as in claim 1, wherein the inner sheath is retractably mounted over the expandable tubular mesh to constrain the tubular mesh in the constrained configuration, and wherein the inner sheath may be distally advanced to engage the proximal end of the tapered tip to circumscribe and constrain the expandable tubular mesh and may be proximally retracted to release the expandable tubular mesh from constraint so that the mesh self-expands into the expanded configuration.

10. The clot extraction catheter as in claim 1, further comprising an inner pusher tube advancable within the inner sheath.

11. The clot extraction catheter as in claim 10, wherein the pusher tube comprises a guidewire lumen.

12. A system for extracting clot from a blood vessel, the system comprising:
   the clot extraction catheter as in claim 1; and
   a guidewire advancable within the inner sheath of the clot extraction catheter, wherein the guidewire comprises a bulb near a distal end of the guidewire.

13. The system of claim 12, wherein the guidewire comprises a soft, floppy tip distal to the bulb.

14. A method for extracting a clot from a bodily vessel or cavity, the method comprising:
   positioning a distal end of a tapered tip of a clot extraction catheter in a lumen of the bodily vessel or cavity proximal of a clot;
   advancing the tapered tip past the clot such that a proximal end of the tapered tip is distal of the clot;
   opening a ring coupled to a proximal end of a tubular mesh of the clot extraction catheter to open the proximal end of the tubular mesh;
   retracting the tubular mesh proximally to capture the clot within the tubular mesh;
   adjusting an angle of the opened ring relative to a shaft of the clot extraction catheter before or during retracting of the tubular mesh to capture the clot;
   closing the ring to close the proximal end of the tubular mesh and enclose the captured clot within the tubular mesh; and
   removing the clot extraction catheter from the lumen of the bodily vessel or cavity.

15. The method for extracting a clot as in claim 14, wherein adjusting the angle comprises proximally or distally translating a main control wire of the clot extraction catheter coupled to the ring independently from proximally or distally translating at least two chord control wires of the clot extraction catheter.

16. The method for extracting a clot as in claim 15, wherein adjusting the angle comprises proximally or distally translating a first chord control wire of the at least two chord control wires independently from proximally or distally translating a second chord control wire of the at least two chord control wires.

17. The method for extracting a clot as in claim 14, wherein opening the ring coupled to the proximal end of the tubular mesh comprises allowing the ring to self-expand.

18. The method for extracting a clot as in claim 17, wherein allowing the ring to self-expand comprises retracting an inner sheath of the clot extraction catheter over the ring.

19. The method for extracting a clot as in claim 14, wherein closing the ring to close the proximal end of the tubular mesh and enclose the captured clot within the tubular mesh comprises retracting the tubular mesh proximally at least partially into a lumen of the inner sheath.

20. The method for extracting a clot as in claim 19, wherein closing the ring to close the proximal end of the tubular mesh and enclose the captured clot within the tubular mesh comprises one or more of advancing an outer sheath over the inner sheath and the tubular mesh having the captured clot therein or retracting the inner sheath and the tubular mesh having the captured clot therein proximally into a lumen of the outer sheath.

21. The method for extracting a clot as in claim 14, wherein positioning the distal end of the tapered tip of a clot extraction catheter in the lumen of the bodily vessel or cavity proximal of a clot comprises distally advancing the clot extraction catheter with a pusher tube.

22. The method for extracting a clot as in claim 14, wherein positioning the distal end of the tapered tip of a clot extraction catheter in the lumen of the bodily vessel or cavity proximal of a clot comprises advancing a guidewire through the bodily vessel or cavity and advancing the clot extraction catheter over the guidewire.

23. The method for extracting a clot as in claim 14, wherein the bodily vessel or cavity comprises a blood vessel.

24. The method for extracting a clot as in claim 23, wherein the blood vessel is selected from the group comprising a vein, an artery, the aorta, a pulmonary artery, a vena cava, an inferior vena cava (IVC), a superior vena cava (SVC), an internal jugular vein, an external jugular vein, a subclavian vein, a hepatic vein, a renal vein, an iliac vein, a common iliac vein, an internal iliac vein, an external iliac vein, a femoral vein, and a peripheral vein.

* * * * *